United States Patent
Konukoglu et al.

(10) Patent No.: US 12,247,328 B2
(45) Date of Patent: Mar. 11, 2025

(54) COMPOSITE CORE YARN, ARTICLE OF CLOTHING COMPRISING A COMPOSITE CORE YARN, METHOD FOR PRODUCING A COMPOSITE CORE YARN AND USE OF A COMPOSITE CORE YARN

(71) Applicant: SANKO TEKSTIL ISLETMELERI SAN. TIC. A.S., Gaziantep (TR)

(72) Inventors: Hakan Konukoglu, Gaziantep (TR); Goekhan Aydin, Gaziantep (TR)

(73) Assignee: SANKO TEKSTIL ISLETMELERI SAN. TIC. A.S., Gaziantep (TR)

( * ) Notice: Subject to any disclaimer, the term of this patent is extended or adjusted under 35 U.S.C. 154(b) by 181 days.

(21) Appl. No.: 16/957,084

(22) PCT Filed: Dec. 21, 2018

(86) PCT No.: PCT/EP2018/086696
§ 371 (c)(1),
(2) Date: Jun. 22, 2020

(87) PCT Pub. No.: WO2019/122378
PCT Pub. Date: Jun. 27, 2019

(65) Prior Publication Data
US 2020/0347527 A1    Nov. 5, 2020

(30) Foreign Application Priority Data
Dec. 22, 2017    (EP) ..................................... 17210449

(51) Int. Cl.
*D02G 3/44*      (2006.01)
*A41D 1/00*      (2018.01)
(Continued)

(52) U.S. Cl.
CPC ............... *D02G 3/441* (2013.01); *D02G 3/12* (2013.01); *D02G 3/32* (2013.01); *D02G 3/36* (2013.01);
(Continued)

(58) Field of Classification Search
None
See application file for complete search history.

(56) References Cited

U.S. PATENT DOCUMENTS

2010/0108225 A1    5/2010    Lamontia et al.
2014/0024868 A1    1/2014    Lai et al.
(Continued)

FOREIGN PATENT DOCUMENTS

CN      1671901      *    9/2005
CN      102312307 A      1/2012
(Continued)

OTHER PUBLICATIONS

Machine translation of JPH11168268 (Year: 1999).*
(Continued)

*Primary Examiner* — Shawn Mckinnon
(74) *Attorney, Agent, or Firm* — McCoy Russell LLP

(57) ABSTRACT

The present invention provides a composite core yarn comprising at least two conductive filaments as a core and a cover layer which encapsulates the core. For providing an adaptable composite core yarn, the cover layer comprises staple fibers. A woven fabric comprising the composite core yarn as well as an article of clothing comprising the composite core yarn is provided together with a method of producing the composite core yarn and a description of different utilizations of the composite core yarn in different applications is likewise provided.

12 Claims, 3 Drawing Sheets

(51) Int. Cl.
  *A61B 5/024* (2006.01)
  *D02G 3/12* (2006.01)
  *D02G 3/32* (2006.01)
  *D02G 3/36* (2006.01)

(52) U.S. Cl.
  CPC .......... *A41D 1/002* (2013.01); *A61B 5/02438* (2013.01); *A61B 2560/0462* (2013.01); *D10B 2401/16* (2013.01); *D10B 2401/18* (2013.01); *D10B 2501/00* (2013.01); *D10B 2509/00* (2013.01)

(56) References Cited

U.S. PATENT DOCUMENTS

| | | | |
|---|---|---|---|
| 2014/0170919 | A1 | 6/2014 | Manipatruni et al. |
| 2017/0143977 | A1* | 5/2017 | Kaib ..................... A61N 1/046 |

FOREIGN PATENT DOCUMENTS

| | | | |
|---|---|---|---|
| CN | 102312307 | B | 4/2014 |
| CN | 200981909 | * | 2/2016 |
| EP | 2505090 | A2 | 10/2012 |
| JP | H11168268 | * | 6/1999 |
| JP | 2017089052 | * | 5/2017 |
| KR | 20140017335 | A | 2/2014 |
| RU | 2206649 | C1 | 6/2003 |
| WO | 9841279 | A1 | 9/1998 |
| WO | 9964657 | A2 | 12/1999 |
| WO | 0198572 | A2 | 12/2001 |
| WO | 03104538 | A1 | 12/2003 |
| WO | 2006102560 | A1 | 9/2006 |
| WO | 2007050650 | A2 | 5/2007 |
| WO | 2008130563 | A1 | 10/2008 |
| WO | 2009020274 | A1 | 2/2009 |
| WO | 2009037631 | A1 | 3/2009 |
| WO | 2010045155 | A2 | 4/2010 |
| WO | 2012073230 | A1 | 6/2012 |
| WO | 2012140079 | A1 | 10/2012 |
| WO | 2014041032 | A1 | 3/2014 |
| WO | 2014092781 | A1 | 6/2014 |
| WO | 2014192002 | A1 | 12/2014 |
| WO | 2015115441 | A1 | 8/2015 |
| WO | 2016073655 | A2 | 5/2016 |
| WO | WO2016131936 | * | 8/2016 |
| WO | 2017020112 | A1 | 2/2017 |
| WO | 2017051378 | A1 | 3/2017 |
| WO | 2018202905 | A1 | 11/2018 |

OTHER PUBLICATIONS

Machine translation of JP2017089052 (Year: 2017).*
Machine translation of CN200981909 (Year: 2016).*
Machine Translation of CN1671901 (Year: 2005).*
Machine Translation of WO2016131936 (Year: 2016).*
ISA European Patent Office, International Search Report Issued in Application No. PCT/EP2018/086696, Mar. 21, 2019, WIPO, 5 pages.
Japanese Patent Office, Office Action Issued in Application No. 2020-554932, Sep. 28, 2021, 10 pages.
European Patent Office, Office Action Issued in Application No. 22179817.6, Sep. 23, 2024, Germany, 4 pages.

* cited by examiner

COMPOSITE CORE YARN, ARTICLE OF CLOTHING COMPRISING A COMPOSITE CORE YARN, METHOD FOR PRODUCING A COMPOSITE CORE YARN AND USE OF A COMPOSITE CORE YARN

CROSS-REFERENCE TO RELATED APPLICATIONS

The present application is a U.S. National Phase of International Patent Application Serial No. PCT/EP2018/086696 entitled "COMPOSITE CORE YARN, ARTICLE OF CLOTHING COMPRISING A COMPOSITE CORE YARN, METHOD FOR PRODUCING A COMPOSITE CORE YARN AND USE OF A COMPOSITE CORE YARN," filed on Dec. 21, 2018. International Patent Application Serial No. PCT/EP2018/086696 claims priority to European Patent Application No. 17210449.9 filed on Dec. 22, 2017. The entire contents of each of the above-referenced applications are hereby incorporated by reference for all purposes.

TECHNICAL FIELD

The present invention relates to a composite core yarn which has electric conductivity.

BACKGROUND AND SUMMARY

Yarns which have electric conductivity may be used in various fields such as clothing applications or in the semiconductor industry.

US 2014/0242868 A1 describes an electrically conductive yarn used for textiles wherein staple and metal fibers are mixed, which mixture then forms the yarn.

In the field of electronics, electrically conductive yarns are e.g. disclosed in US 2014/0170919 A1 and WO 2014/092781 A1.

In US 2014/0170919 A1, a core is provided which is encapsulated by first and second electrically conductive layers surrounding the core. This encapsulated wire is also encapsulated by a conventional polymer layer, to provide electric isolation.

In WO 2014/092781 A1 metallic filaments are provided, which are embedded in an insulation material, which is encapsulated by a polymer layer to provide an electric isolation.

A further yarn which is an elastic ring spun yarn, is disclosed in EP 2 145 034 B1. To create a natural feeling in combination with high stability and endurance, an elastic core filament is provided, around which further filaments may be twisted by ring spinning. This twisted core is encapsulated by so-called staple fibers, which are made of natural materials, to provide a natural feeling to the yarn.

The present invention provides a high performance yarn having an improved electric conductivity combined with adaptable surface optic and/or haptic aspects.

In order to solve the aforementioned problem, according to a first arrangement a core yarn with at least two electrically conductive filaments as a core and a cover layer which encapsulates the core is provided. The cover layer include staple fibers and the core includes an elastic filament having an elasticity in at least a longitudinal direction thereof.

This core yarn is discriminated over the closest prior art, which is WO 2014/092781 A1, in that a cover layer comprising staple fibers is provided. Such staple fibers are distinct fibers which have a certain length. The staple fibers may comprise a plurality of different lengths. Such staple fibers in textile technology are named non-continuous fibers for differentiating these fibers from so-called continuous filament fibers. These filaments may have an indefinite length.

By providing a cover layer, comprising staple fibers or, which is preferable, constituted by staple fibers, the encapsulation of the electrically conductive filaments which serve as the core, ensures the adaptability of the surface properties of the core yarn.

Depending on the utilization of the yarn it may also be enough to provide only one electrically conductive filament instead of at least two electrically conductive filaments. This is in particular the case it the filament is constituted by the later described coated filament, which may have a non-electrically conductive core and an electrically conductive cover layer.

According to a further arrangement, the core of the composite core yarn may further comprise an elastic filament having elasticity in the longitudinal direction. Elasticity is the ability to deform reversibly under stress. By combining the elasticity with an electric conductivity, the endurance of the yarn can be further improved. In particular, forces may act in longitudinal direction without breaking the complete yarn.

The elasticity may have a young modulus (in GPa) of 0.01 to 5, more preferably 0.01 to 0.5 in particular, 0.01 to 0.1. Alternatively or additionally the elongation from a relaxed state to a state, where the yarn is expanded to the maximum where a reversible contraction can still occur. Further preferred elongations are: 2%, 3%, 4%, 6%, 8%, 10%, 13%, 15%, 18%, 20%, 50%, 100%, 200%, 300%, 400%. The aforementioned values may each separately serve as lower or upper borders.

According to a further arrangement, the elastic filament may be a separate filament which is not constituted by the at least two conductive filaments. Hence, the composite core yarn at least comprises three filaments which at least three filaments make up the core which is embedded in the cover layer comprising staple fibers. By combining at least one, or preferably only one elastic filament, with at least two electrically conductive filaments, the endurance of the yarn can be improved since the stretch abilities are good which reduces the probability that the conductivity of the yarn is distorted if one electrically conductive filament breaks, as there is still a second electrically conductive filament present. While it is advantageous that the electrically conductive filaments are made of a different material and/or constitution, electrically conductive filaments having the same composition and/or constitution are usable as well.

Alternatively or additionally, the at least one of the electrically conductive filaments may have a respective elasticity to also constitute the elastic filament. In this case the presence of a further non electrically conductive filament in the core can be omitted.

The electing of at least three filaments provides further possibilities for the adaptability of the composite core yarn. According to a further arrangement, the at least two conductive filaments are wound around the elastic filament. This may be done by a ring spinning technique as is described in EP 2 145 034 B1. When the respective electrically conductive filaments are wound around the elastic filament, there is the advantage that the electrically conductive filaments, which may be filaments having no substantial elasticity, are able to expand in length and not be broken by expansion. When, for example, the electrically conductive filaments are aligned in parallel with respect to each other in the longitudinal direction in the core and not wound around an elastic filament or any other filament, the breakage probability that at least one electrically conductive filament is broken, increases in comparison with the situation where the respective electrically conductive filaments are wound around the elastic filament.

The at least two conductive filaments may be selected from the group of the following: a) a metal filament made of a metallic material, and b) a coated filament. The coated filament may have a core of a substantially not electrical conducting material and a surface layer of an electrical conductive material. It is advantageous that one of the at least two filaments is the metal filament and that the at least second of the filaments, is the coated filament. By having the different types of electrically conductive filaments, the physical property of the composite core yarn may be tuned.

In particular, by combining an electrically conducting coating with a non-electrical conductive core, the core material basically defines the elongation properties of the filament while the respective coating defines the electric conduction properties. Conversely thereto, when a metal filament is used, this metal filament is very susceptible to breaking which is not the case for the coated filament.

The coated filament may simultaneously provide the elasticity to simultaneously constitute the elastic filament. In this case, the presence of a further elastic filament can be omitted. This coated filament having electric conductivity and elasticity may also be provided as a single filament which is encapsulated by staple fibers as an alternative to the aforementioned inventive composite core having the at least two conductive filaments as a core material.

According to a further arrangement, the composite core yarn is a ring spun core yarn.

In such ring spinning, the filaments and/or also the staple fiber material which may be supplied as roving, is fed e.g. in drafting rollers and thereafter spun and wound around a rotating spindle. Further details concerning the ring spinning are described in EP 2 145 034 B1, in particular [0049] to [0053] and FIG. 4 thereof, which disclosure is incorporated herein by reference.

The staple fibers may comprise at least one or a mixture of fibers from the group of: natural, recycled and/or synthetic fibers and/or fibers made of the following materials: cotton, viscose, polyester, wool, linen, alpaca, vicuna, angora, cashmere, kapok, manila, flax, hemp, ramie, hessian, sisal, coir, asbestos, glass, azlon, acetate, triacetate, acryl, aramid, nylon, olefin, which are used to form the cover layer, can be selected from the following: cotton, viscose, polyester, wool, linen, alpaca, vicuna, angora, cashmere, kapok, manila, flax, hemp ramie, jute, sisal, coir, asbestos, glass, azlon, acetate, triacetate, acryl, aramid, nylon, olefin. The respective fibers made of the aforementioned material may be used as a single material fiber mixture or a composition of any one of the aforementioned different material fibers in one of different lengths. The respective fibers may be natural fibers, synthetic fibers and/or recycled fibers.

The metal which forms the metal filament or the electrically conductive material of the surface layer of the coated filament may be selected from the following elements or alloys thereof: copper, silver, iron, gold, magnesium, steel. Any other electrically conductive metal or metal alloy may also be utilized.

The respective non-electrically conductive material constituting the core of the coated filament may be selected from the following: polyamide (PA), Polyethersulfon (PES), Polybutylenterephthalat (PBT), Polyethylenterephthalat (PET) and a combination thereof.

The metal filament may have a thickness of 0.0001 micron to 1.500 micron. Further preferred thicknesses are: 0.0010 micron, 0.0100 micron, 0.1000 micron; 0.5000 micron, 1.0000 micron, or any sum or difference of one or more of the aforementioned values. The aforementioned values may each separately serve as lower or upper borders of a thickness range. The thickness on the one hand defines the conductivity as well as the probability that the yarn breaks. Therefore, the selection of the respective metal filament thickness in the aforementioned ranges depends on the desired properties of the final core yarn.

The thickness of the coated filament and/or the thickness of the elastic filament may be between 1 or 5.498 denier. Further preferred thicknesses are: 1.500 denier, 1.800 denier, 2.500 denier, 3.000 denier, 4.400 denier, 5.000 denier. The aforementioned values may each separately serve as lower or upper borders of a thickness range.

Denier is a unit of measurement for the linear mass density of fibers in grams per 9.000 meters of the fiber. This means that 1 denier is 1 gram per 9.000 meters. In other words, denim is measured in mass of yarn in g per 9000 meters.

The core yarn itself, which may have the cover layer of staple fibers and at least two filaments, has a thickness preferably between 1 and 6.000 denier. Further preferred thicknesses are: 1.500 denier, 1.800 denier, 2.500 denier, 3.000 denier, 4.400 denier, 5.000 denier. The aforementioned values may each separately serve as lower or upper borders of a thickness range.

According to a further aspect, a woven fabric is provided which comprises the composite core yarn described in the foregoing section. In particular, the composite core yarn may constitute the warp and/or weft yarn of the woven fabric.

However, the present invention is not delimited to woven fabrics. Also other fabrics like knitted fabric, or non-woven fabrics can contain the yarn as a component or may be completely set up of this yarn. The inventive yarn may be used in circular knitted and/or in flat knitted fabrics.

A knitted fabric comprising the inventive composite core yarn may also be provided.

According to a further aspect, an article of clothing is provided which comprises the aforementioned composite core yarn.

The article of clothing includes shoes, t-shirts, jackets, but however, first layer clothing such as socks, underwear, and t-shirts are preferred because the functionality of the articles with the electric conductivity may then provide a better transmission/contact with the human body, when a human being wears the respective article. However, the article of clothing is not delimited thereto and may be any article of clothing.

In the article of clothing, one or more wire paths may be provided. The wire path is comprised of the composite core yarn or may be in particular constituted by the composite core yarn, having a configuration which is described in the foregoing section.

The wire path may extend within the woven fabric or may be embroidered on the material of which the article of clothing is made.

The wire path may be a distinctive path which extends from one specific location of the clothing to a second specific location of the clothing to allow the selective transfer of signals between the respective two locations.

The respective article of clothing may have one or more electrodes which are connected to a respective end of one wire path and the other end of the wire path may be connectable to a control station, which control station is adapted to communicate with the electrode.

By doing so it is not necessary to provide distinct, commonly known cables from the location where the control station is mounted to the location where the electrodes which may serve as sensors for sensing body functions.

Each respective wire path may have an electrically non-conductive coating which prevents the transfer of the electric current in the radial direction of the wire path to the surrounding area.

A pocket for containing the respective control station may be incorporated in the clothing. The control station may be connected to respective terminals which are provided at ends of the respective wire paths to transfer signals via the wire paths to the electrodes.

The electrodes may be electrode pads. Electrode pads may be patches of a conductive material, for example, a woven or non-woven textile material which is integrally formed in the article of clothing.

The article of clothing may have a plurality of wire paths which are connected to respective electrodes wherein at least one electrode is positioned in the region of the human heart and at least a further electrode is positioned at an extremity of the human body, for example at one or both shoulders, and/or at one or both hips and/or at one or both knees, and/or at one or both feet, and/or at one or both hands. With such a constitution, physical functions, in particular, heart functions may be measured.

It is preferred that the respective article of clothing has a certain compression functionality and thus is a piece of compression clothing as otherwise the respective interaction of the sensors/electrodes and the human body is probably not sufficient for receiving good signals to track the physical activity of the human body.

The control station may be adapted to supply an electric current to the electrodes and to receive information from the electrodes to display a physical activity of the human body.

According to a further aspect, a method is provided for producing a composite core yarn.

The method comprises the steps of supplying at least two electrically conductive filaments as a core, supplying staple fibers, and ring-spinning the at least two electrically conductive filaments with the staple fibers such that the cover layer which comprises the staple fibers encapsulates the core to form the conductive yarn. However, all other possible methods for producing such a composite core yarn are not excluded by this inventive method.

Examples of such spinning methods are ring spinning, open end spinning and air jet spinning. However, in particular the utilization of a ring spinning method is advantageous.

The use of the aforementioned composite core yarn is disclosed for at least one of the following aspects: use in mobile devices, use in sensor elements, use as filter elements, use in health care facilities, use for microwave applications, use in sportswear, use in health gear, use in smart textiles and use in gloves and for use in soft rooftops for convertible automobiles. Further areas of utilization are any areas where the following technical functions are advantageous conductive properties, anti-static properties, anti-bacterial properties, anti-fungal properties, and electromagnetic shielding properties.

For facilitating the understanding of the invention, some specific embodiments are explained in the following which, however, do not limit the scope of the general description.

The respective features, which are mentioned in the foregoing, and the distinct features outlined in the following with respect to the specific examples may be combined with each other in any form.

DETAILED DESCRIPTION

Figure 2:
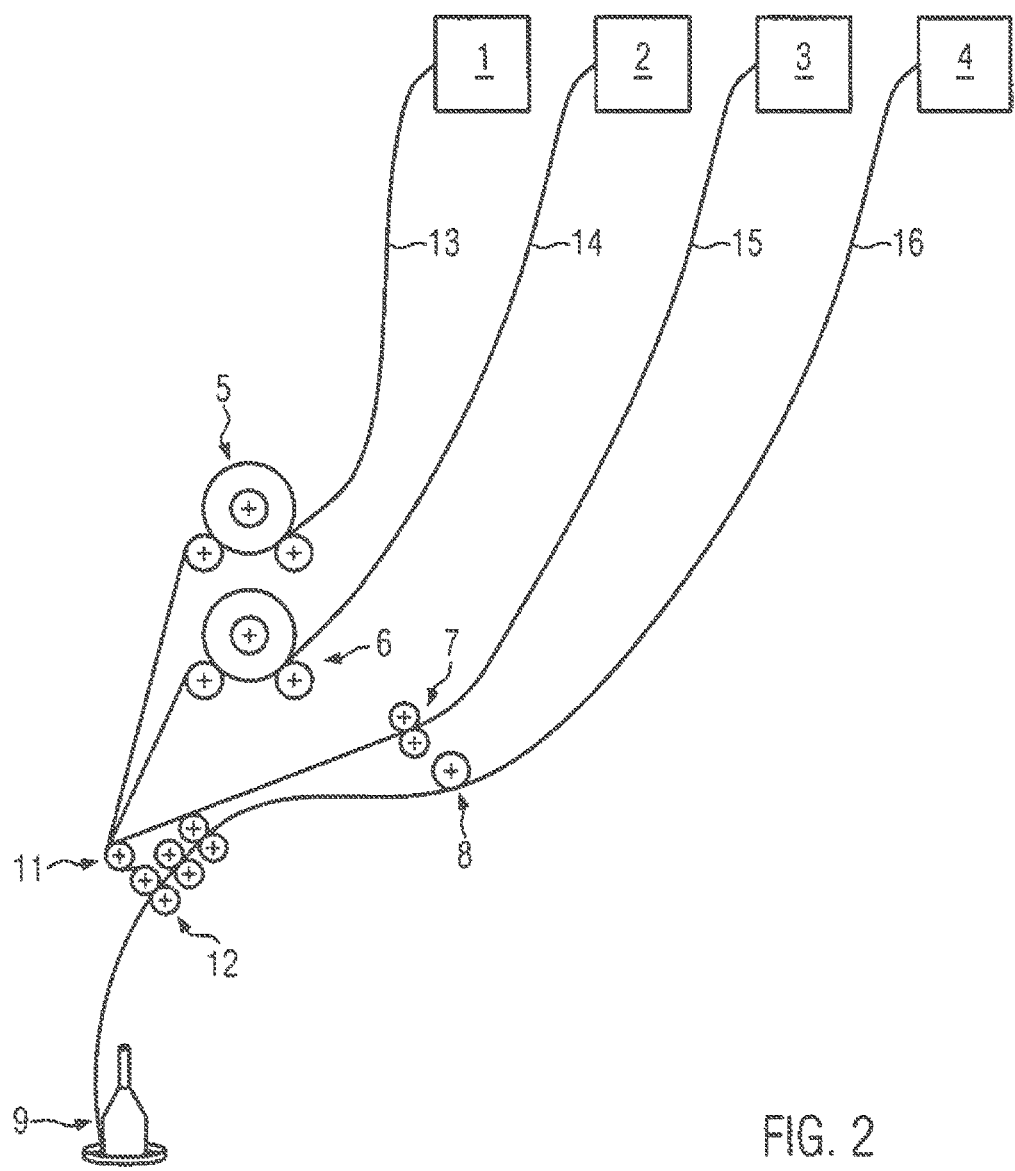
FIG. 2 shows an example of a ring spinning machine and process to form the core yarn shown in FIG. 1.

A sketch of a ring spinning machine is shown in FIG. 2. Reference numbers 1 to 4 as denoted in FIG. 2 are bobbins from which the roving 16 (bobbin having reference number 4) or filaments (bobbins having reference numbers 1, 2 and 3) are supplied to a respective drafting 5, 6, 7, 8 stage which comprises drafting rollers.

The roving or filament are supplied from the bobbins 1, 2, 3, and 4 to the drafting rollers contained in a respective drafting stage 5, 6, 7, 8, where the material is drafted between the drafting rollers. From the stage the drafted material is supplied to a spindle 9 (ring spinning spindle).

The respective set up shown in FIG. 2 is not intended to delimit the invention. However, the respective bobbins 1, 2, 3, 4 as well as the respective drafting stages 5, 6, 7, 8 each may be provided one after each other and adjacent to each other in the horizontal or in the vertical direction.

Moreover it should be noted, that in FIG. 2 there is only shown one section for production gone single inventive yarn. However, two or more of said sections may be placed one after each other in the horizontal direction. Each section may be one unit wherein a plurality of units may be provided one subsequent to the other to make a plurality of yarns simultaneously.

Figure 3:
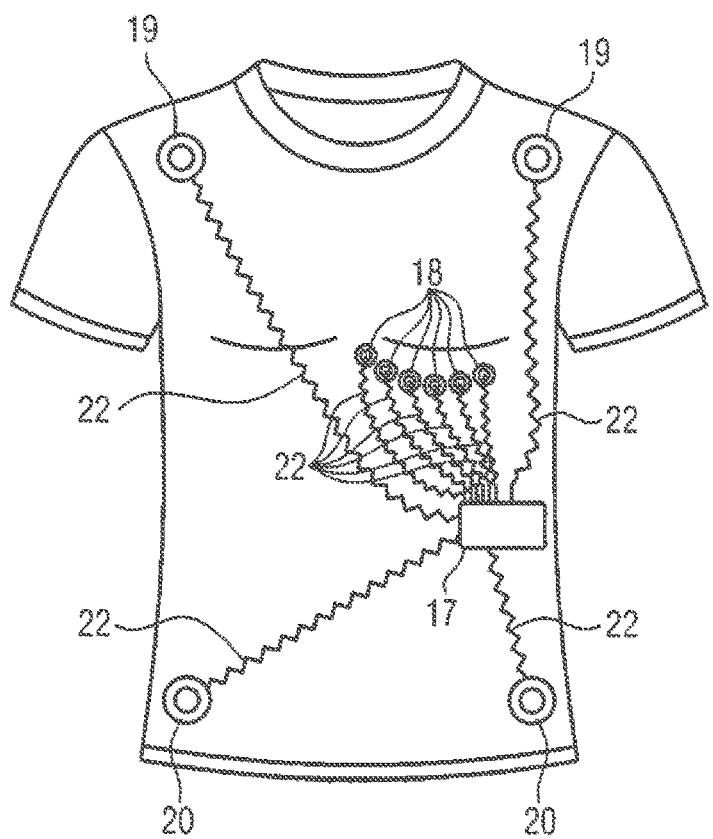
FIG. 3 shows an example of an article of clothing which is a compression t-shirt in which wire paths constituted by composite core yarn of FIG. 1 are provided.

Between the drafting stage and the spindle in the present stage a twisting stage 11 is provided wherein in the present arrangement shown in FIG. 3 the filaments 13, 14, and 15 from the bobbins 1, 2 and 3 are first wound around each other and, thus, twisted.

Downstream of the twisting stage 11 and upstream of the spindle 9 there is an encapsulation stage 12 provided wherein the respective roving 16, comprising the staple fibers, is made to form the cover layer encapsulating the twisted core, which is constituted by the filament 13, 14 and 15.

In the example shown in FIG. 2, the respective filament having reference sign 13 is a metal filament which is made of a metal material, the filament having reference sign 14 is a coated filament having a core of a substantially not electrically conductive material and a surface layer of an electric conductive material and the filament with reference sign 15 is an elastic filament having a certain elasticity in at least the longitudinal direction.

In the case in FIG. 2, the respective metal filament 13 and the coated filament 14 are wound around the elastic filament 15 in the twisting stage 11.

Thereafter, the roving, comprising the staple fibers, is provided in the encapsulation stage 12 to form an encapsulating cover layer to the core which is made up of the metal filament 13, the coated filament 14 and the elastic filament 15.

Although in the present case, a ring spinning is described, the preparation of the composite core yarn is not delimited to the method of ring spanning, but can be made by any method which is able to provide a cover layer which encapsulates the core which comprises one or more filaments. Alternatives of such ring spinning methods are open end spinning and air jet spinning The example shown in the present case has a twisted core. However, the filaments in the core are not necessarily twisted, they can e.g. extend in parallel with respect to each other as well.

Although in the present case there is provided the metal filament 13, the coated filament 14 and the elastic filament 15 this is not essential.

The at least two conductive filaments may be selected from the group of the following: a) a metal filament made of a metallic material, and b) a coated filament. The coated filament may have a core of a substantially not electrical conducting material and a surface layer of an electrically conductive material. It is advantageous that one of the at least two filaments is the metal filament and that the at least second of the filaments is the coated filament. By having the different types of electrically conductive filaments, the physical properties of the composite core yarn may be adapted.

The elastic filament may be a separate filament which is not constituted by the at least two conductive filaments. Hence, the composite core yarn at least comprises three filaments which at least three filaments make up the core which is embedded in the cover layer comprising staple fibers. By combining at least one, or preferably only one elastic filament with at least two electrically conductive filaments, the endurance of the yarn can be improved, as the stretch abilities are good, and the probability that the conductivity in the yarn is distorted if one electrically conductive filament breaks, is reduced as there is still a second electrically conductive filament present. It is advantageous that the electrically conductive filaments are made of a different material and/or constitution, but however also electrically conductive filaments having the same composition and/or constitution are useable.

Staple fibers in the meaning of the present invention are fibers or clusters of fibers which have a single or different length. Conversely thereto, a filament is a single fiber having a substantially indefinite length.

This explanation corresponds to the understanding of "staple fiber" and "filament" in the textile industry.

Figure 1A:
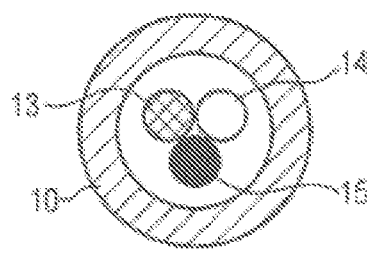
FIG. 1A shows a cross-section of a first arrangement of a composite core yarn.
Figure 1B:
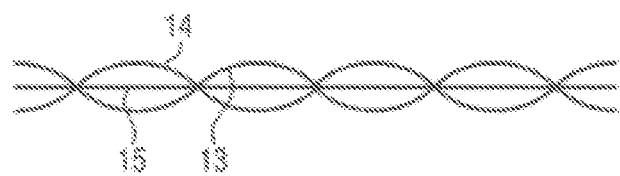
FIG. 1B, shows a view along the longitudinal direction of the core of the composite core yarn shown in FIG. 1A.

A composite core yarn which is generated by ring spinning, as described with reference to FIG. 2, is shown in FIG. 1A and FIG. 1B.

In FIG. 1B, the inner center of the core of the composite core yarn is constituted by the elastic filament 15 while the respective electrically conductive filaments 13, 14, in particular the metal filament 13 and the coated filament 14, is wound around the elastic filament.

However, such a respective spiral wound of the at least two conductive filaments about the elastic filament, is not necessary. At least a composite core yarn is provided which has as a core, at least two electrically conductive filaments. They may be extended in parallel to each other or wound around each other, with or without a combination of a further independent elastic filament.

However, one of the respective electrically conductive filaments, or two of the elastically conductive filaments may provide elasticity such that there is no necessity to provide at least a third filament having the desired elasticity.

Such an elastic filament may also be provided by a coated filament configuration having a core of a substantially not electrically conductive material which is however preferably elastic in its longitudinal direction. The surface layer of an electrically conductive material may be a metal which is per se not elastic. The provision of two electrically conductive filaments prevents the danger that there is no conductivity if the respective one of the electrically conductive filaments is broken.

The staple fibers may comprise at least one or a mixture of fibers from the group of: natural, recycled and/or synthetic fibers and/or fibers made of the following materials: cotton, viscose, polyester, wool, linen, alpaca, vicuna, angora, cashmere, kapok, manila, flax, hemp, ramie, hessian, sisal, coir, asbestos, glass, azlon, acetate, triacetate, acryl, aramid, nylon, and olefin. The fibers which are used to form the cover layer can be selected from the following: cotton, viscose, polyester, wool, linen, alpaca, vicuna, angora, cashmere, kapok, manila, flax, hemp ramie, jute, sisal, coir, asbestos, glass, azlon, acetate, triacetate, acryl, aramid, nylon, and olefin. The respective fibers made of the aforementioned material may be used as a single material fiber mixture or a composition of any one of the aforementioned different material fibers in one or different lengths. The respective fibers may be natural fibers, synthetic fibers, and/or recycled fibers.

The metal which forms the metal filament 13 or the electrically conductive material of the surface layer of the coated filament 14, may be selected from the following elements or alloys thereof: copper, silver, iron, gold, magnesium, steel.

The respective non-electrically conductive material constituting the core of the coated filament 14 may be selected from the following: polyamide (PA), Polyethersulfon (PES), Polybutylenterephthalat (PBT), Polyethylenterephthalat (PET) and a combination thereof.

The metal filament 13 may have a thickness of 0.0001 micron to 1.500 micron. Further preferred thicknesses are: 0.0010 micron, 0.0100 micron, 0.1000 micron, 1.000 micron, or any sum or difference of one or more of the aforementioned values.

The aforementioned values may each separately serve as lower or upper borders of a thickness range. The thickness on the one hand defines the conductivity as well as the probability that the yarn breaks. Therefore, the selection of the respective metal filament thickness in the aforementioned ranges depends on the desired properties of the final core yarn.

The thickness of the coated filament 14 and/or the thickness of the elastic filament 15 may be between 1 or 5.498 denier. Further preferred thicknesses are: 1.500 denier, 1.800 denier, 2.500 denier, 3.000 denier, 4.400 denier, 5.000 denier. The aforementioned values may each separately serve as lower or upper borders of a thickness range.

Denier is a unit of measurement for the linear mass density of fibers in grams per 9.000 meters of the fiber. This means that 1 denier is 1 gram per 9.000 meter.

The core yarn itself, which may have the cover layer of staple fibers and at least two filaments, has a thickness preferably between 1 and 6.000 denier. Further preferred thicknesses are: 1.500 denier, 1.800 denier, 2.500 denier, 3.000 denier, 4.400 denier, 5.000 denier. The aforementioned values may each separately serve as lower or upper borders of a thickness range.

In the embodiment shown in FIG. 2, first the respective elastic filament 15 is twisted together with the metal filament 13 and the coated filament 14 before the encapsulation with the staple fibers is done. However, any further, alternative sequence may be used. For example, only two fibers may be twisted or only a single fiber may be encapsulated by the staple fibers. It is also shown in this figure that one of the electrically conductive filaments is a metal filament and that the other filament is a coated electrically conductive filament, this is also not essential and any combination thereof also more than two electrically conductive filaments can be used which can be wound around an elastic filament or which may be aligned in parallel to each other.

This composite core yarn may be used for providing one or more electric paths 22 in an article of clothing.

An example of such an article of clothing is the t-shirt shown in FIG. 3.

Other examples of articles of clothing, for instance, shoes, gloves, socks, underwear, t-shirts, pullovers and jackets may also be used. However, first layer clothing such as socks, underwear, and t-shirts are preferred, because the functionality of the articles with the electric conductivity may then provide a better transmission/contact with the human body, when a human being wears the respective article. However, the article of clothing is not delimited thereto and may be any article of clothing.

It is shown in FIG. 3 that there are provided in total 10 electrically conductive paths 22 which connect a respective control station 17 with respective electrodes 18, 19, 20. The group of electrodes having reference sign 18, are provided on the t-shirt in a region of the heart of a human being. The respective electrodes having reference sign 19 are provided at the extremities of the main body, in particular, at both front sides of the shoulders. The respective electrodes having reference sign 20 are provided at the extremities of the main body, in particular, at both and both front sides of the hips.

Between the respective electrodes which are made in the present embodiment as electrode pads, and the control station 17, signals can be transferred via the wire paths 22. Thus, a physical activity of the heart or any other physical activity may be measured.

The electrode pads may be made of an electrically conductive material, also a woven or non-woven material which is integrally formed in the material of the t-shirt or the article of clothing itself.

The respective control station 17 may be mounted deconnectably from respective plug/s which are provided at the ends of the wire paths 22.

The respective control station 17 may be provided in a pocket 21 of the clothing.

Via an Application (App) on a mobile device, the respective control station 17 may be controlled e.g. by means of wireless communication.

The respective wire path may be encapsulated in a nonconductive material such that a non-conductive coating prevents a transfer of an electric current between the wire path core and the radial surrounding area.

In particular, the wire path may be embroidered in the article of clothing. However, any other attachments to the article of clothing are also possible.

This example concerning the t-shirt is only one example where the composite core yarn may be used in applications. Other applications are: use in mobile devices, use in sensor elements, use as filter elements, use in health care facilities, use for microwave applications, use in sportswear, use in health gear, use in smart textiles and use in gloves and for use in soft rooftops for convertible automobiles.

REFERENCE SIGN LIST 1, 2, 3, 4 Bobbin
5, 6, 7, 8 Drafting stage
9 Spindle
10 Cover layer
11 Twisting stage
12 Encapsulation stage
13 Metal filament
14 Coated filament
15 Elastic filament
16 Roving
17 Control station
18 Electrode
19 Electrode
20 Electrode
21 Pocket
22 Wire path

The invention claimed is:

1. An article of clothing comprising one or more wire paths comprising a composite core yarn, wherein each wire path is connected between an electrode mounted on an inner surface of the article of clothing and a control station, the control station being spaced away from and being in communication with the electrode, where the one or more wire paths have an electrically non-conductive coating which prevents a transfer of an electric current between a wire path core and a surrounding area thereof;
  wherein the composite core yarn comprises a core and a cover layer encapsulating the core, the cover layer comprising staple fibers, and wherein the core consists of three separate filaments,
  which are two electrically conductive filaments and one elastic filament, wherein one electrically conductive filament of the two electrically conductive filaments is a coated filament having a filament core of a non-electrically-conductive material,
  wherein the filament core has an elasticity in at least longitudinal direction thereof, such that the coated filament constitutes an elastic filament, and wherein one electrically conductive filament of the two electrically conductive filaments is a metal filament consisting of metal,
  wherein the metal is selected from the group consisting of copper, silver, iron, gold, magnesium, and steel,
  wherein the staple fibers are distinct fibers of a finite length,
  wherein the composite core yarn is a ring spun yarn, and wherein each wire path is embroidered on the article of clothing.

2. The article of clothing of claim 1, wherein the article of clothing further comprises at least one electrode mounted on the inner surface thereof, such that the at least one electrode is configured to contact a human body's skin directly or indirectly; and a pocket, configured to receive the control station, which communicates with the at least one electrode via a wire path of the one or more wire paths.

3. The article of clothing of claim 1, wherein a plurality of wire paths are provided which are connected to a respective electrode, wherein a first electrode is adapted to be in a region of a human being's heart, and a second electrode is adapted to be positioned at an extremity of the human being, away from the region of the heart.

4. The article of clothing according to claim 2, wherein the control station is configured to supply the electric current to the at least one electrode and to receive information from the at least one electrode to display a physical activity of a human being.

5. The article of clothing according to claim 1, wherein the elasticity of the elastic filament is in the range of 1 to 500%.

6. The article of clothing according to claim 1, wherein the staple fibers comprise at least one or a mixture of fibers from the group consisting of: natural, recycled and/or synthetic fibers and/or fibers made of: cotton, viscose, polyester, wool, linen, alpaca, vicuna, angora, cashmere, kapok, manila, flax, hemp, ramie, hessian, sisal, coir, asbestos, glass, azlon, acetate, triacetate, acryl, aramid, nylon, olefin.

7. The article of clothing according to claim 1, wherein an electrically conductive material of a surface layer of the coated filament is selected from the group consisting of: copper, silver, steel, iron, gold, magnesium and alloys thereof, or any other electrically conductive metal or metal alloy.

8. The article of clothing according to claim 1, wherein the not electrically conducting material of the core of the coated filament is selected from the group consisting of: polyamide (PA), Polyethersulfon (PES), Polybutylentereph-thalat (PBT), Polyethylenterephthalat (PET) and a combination thereof.

9. The article of clothing according to claim 1, wherein the coated filament has a thickness from 1 denier to 5498 denier.

10. The article of clothing according to claim 1, wherein the composite core yarn has a thickness of 1 denier to 6000 denier.

11. An article of clothing comprising one or more wire paths comprising a composite core yarn, wherein each wire path is connected between an electrode mounted on an inner surface of the article of clothing and a control station, the control station being spaced away from and being in communication with the electrode, and wherein the one or more wire paths have an electrically non-conductive coating which prevents a transfer of an electric current between a wire path core and a surrounding area thereof;

wherein the composite core yarn comprises a core and a cover layer which encapsulates the core, wherein the core consists of two electrically conductive filaments, and wherein the cover layer comprises staple fibers, and wherein a first electrically conductive filament of the two electrically conductive filaments is a coated filament having a filament core of a non-electrically-conductive material, wherein a second electrically conductive filament of the two electrically conductive filaments is a metal filament consisting of metal, wherein the metal is selected from the group consisting of copper, silver, iron, gold, magnesium, and steel, and wherein the filament core has an elasticity in the range of 8% to 300% in at least a longitudinal direction thereof, such that the coated filament constitutes an elastic filament, and wherein the composite core yarn is a ring spun yarn.

12. The article of clothing according to claim 3, wherein the article of clothing is a shirt, wherein the second electrode is positioned at a front side of shoulders of the human being, wherein a third electrode is positioned at a front side of hips of the human being, and wherein the control station is positioned between the heart region and the hips.

* * * * *